Figure 1:
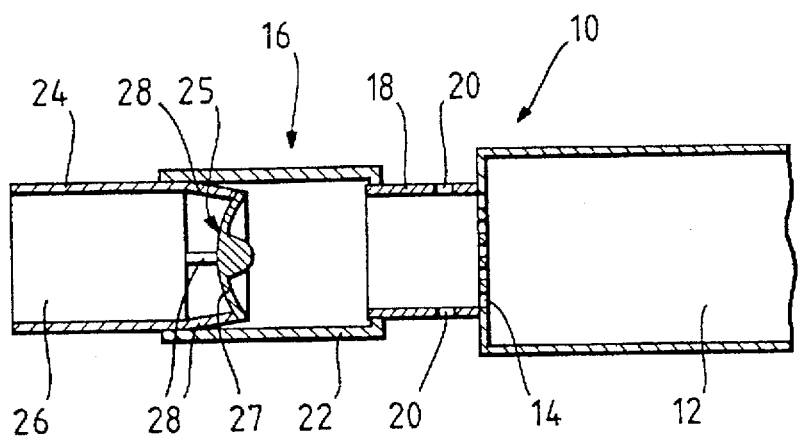

United States Patent

McAughey et al.

[11] Patent Number: 5,724,959
[45] Date of Patent: Mar. 10, 1998

[54] POWDER INHALER WITH SPECIFIC ORIFICE AND BAFFLE ARRANGEMENT

[75] Inventors: John Jackson McAughey, Didcot; John Nigel Pritchard, King's Langley, both of United Kingdom

[73] Assignee: AEA Technology PLC, Didcot, United Kingdom

[21] Appl. No.: 307,290

[22] Filed: Sep. 16, 1994

Related U.S. Application Data

[63] Continuation of Ser. No. 975,949, filed as PCT/GB91/01686, Sep. 30, 1991, abandoned.

[30] Foreign Application Priority Data

Oct. 2, 1990 [GB] United Kingdom .................. 9021433

[51] Int. Cl.⁶ .................. A61M 15/08; A61M 16/00; B05D 7/14; B05D 83/26
[52] U.S. Cl. .................. 128/203.15; 128/203.24; 128/200.18
[58] Field of Search .................. 128/203.15, 203.24, 128/203.23, 203.28, 200.18

[56] References Cited

U.S. PATENT DOCUMENTS

| | | | |
|---|---|---|---|
| 567,558 | 9/1896 | Wiseman | 128/203.24 |
| 2,214,032 | 9/1940 | Stewart | 128/203.15 |
| 2,503,732 | 4/1950 | Heisterkamp | 128/203.15 |
| 2,579,280 | 12/1951 | Trumbour et al. | 128/203.15 |
| 2,581,182 | 1/1952 | Fields | 128/203.15 |
| 2,642,063 | 6/1953 | Brown | 128/203.15 |
| 2,670,739 | 3/1954 | McNeill | 128/200.18 |
| 2,693,805 | 11/1954 | Taplin et al. | 128/203.15 |
| 2,992,645 | 7/1961 | Fowler | 128/203.15 |
| 3,302,374 | 2/1967 | Szekely | 55/226 |
| 3,507,277 | 4/1970 | Altounyan et al. | 128/203.15 |
| 3,518,992 | 7/1970 | Altounyan et al. | 128/203.15 |
| 3,795,244 | 3/1974 | Lax et al. | 128/203.15 |
| 3,837,341 | 9/1974 | Bell | 128/203.15 |
| 3,838,686 | 10/1974 | Szekely | 128/173 |
| 4,739,754 | 4/1988 | Shaner | 128/203.23 |
| 4,945,929 | 8/1990 | Egilmex | 128/200.21 |
| 5,033,463 | 7/1991 | Cocozza | 128/203.23 |

FOREIGN PATENT DOCUMENTS

| | | | |
|---|---|---|---|
| 658437 | 5/1965 | Belgium . | |
| 0069715 | 1/1983 | European Pat. Off. . | |
| 0166294 | 1/1986 | European Pat. Off. . | |
| 0237507 | 9/1987 | European Pat. Off. . | |
| 1118341 | 7/1968 | United Kingdom . | |
| 1404338 | 8/1975 | United Kingdom . | |
| 2064336 | 6/1981 | United Kingdom . | |
| 2129691 | 5/1984 | United Kingdom . | |
| 2142246 | 1/1985 | United Kingdom . | |
| 2151491 | 7/1985 | United Kingdom . | |
| 2248400 | 4/1992 | United Kingdom | 128/203.15 |

*Primary Examiner*—Kimberly L. Asher
*Attorney, Agent, or Firm*—William R. Hinds

[57] ABSTRACT

A dry powder inhaler (10) consists of a chamber (12) into which powder is introduced from a metering system, and a mouthpiece (26) through which a patient inhales, connected by a duct (16), so that air flows through the chamber carrying the powder into the patient's lungs. Within the duct is an impactor (25) consisting of a plate (27) spaced in front of a similarly sized aperture, and between the chamber and the impactor plate is an orifice (18) narrower than the duct, so the air stream is diverted along S-shaped paths to avoid the plate. The presence of the impactor can improve the efficiency of delivery of a drug to the lungs, and decrease the unwanted dose to the mouth and throat, as the latter is principally due to agglomerates or larger particles which are intercepted or broken up by the impactor.

8 Claims, 2 Drawing Sheets

POWDER INHALER WITH SPECIFIC ORIFICE AND BAFFLE ARRANGEMENT

This is a continuation of application Ser. No. 07/975,949 filed as PCT/GB91/01686, Sep. 30, 1991, now abandoned.

This invention relates to an inhaler whereby a drug in the form of a powder may be delivered to a patient.

Inhalers are known which operate solely by the patient breathing in, the inspired air carrying a powder incorporating a drug into the patient's lungs. Examples are the Ventolin Diskhaler and the Ventolin Rotahaler produced by Allen and Hanbury. In both cases the drug powder is delivered into a chamber from an encapsulated form which is punctured. On inspiration, air enters the rear of the chamber and the powder is carried with the inspired air, passing through a grid or lattice with 1.5 mm square holes 1 mm apart, and diluting air enters the sides of the mouthpiece.

A disadvantage of this type of inhaler is that the drug particles tend to agglomerate and that the larger particle sizes so produced do not penetrate to the lung. The lattice through which the aerosol passes is designed to break-up these agglomerates to some degree, but as the airflow only deviates slightly, the majority of particles pass into the mouth of the patient unchanged. Consequently a large fraction of the aerosol consisting of the agglomerates impacts in the area of the mouth and throat, reducing the effective therapeutic dose which is carried to the lung. In addition, a large dose delivered in the mouth/throat area may lead to irritation of the region of impaction.

According to the present invention there is provided a dry powder inhaler comprising a dispensing chamber into which dry powder is introduced in operation, a duct and a mouthpiece through which a patient may inspire, the dispensing chamber being connected via the duct to the mouthpiece; the chamber, the duct and the mouthpiece together defining a flow path such that at least the bulk of the inspired air flows through the chamber, then through the duct, and then through the mouthpiece; wherein there is at least one means within the duct to define at least one orifice forming part of the flow path for air, and for particles of the powder carried by the air, there being a portion of the duct downstream of the orifice and the orifice being of narrower width than that portion of the duct downstream thereof; and means to deviate substantially all the air flow through the orifice abruptly along successive L-shaped paths, whereby larger particles of the powder carried by the air flow undergo impaction due to their inertia whereas smaller particles are carried along with the air flow, the deviating means comprising an impactor in the duct between the said orifice and the mouthpiece, the impactor comprising a stationary plate substantially transverse to the flow direction through the orifice but spaced along the duct from the orifice, of larger projected area than the orifice and of such a shape that any line through the orifice extending parallel to the direction of the air flow at the center of the orifice is obstructed by the plate.

The dimensions of the impactor depend upon the sizes of the particles which it is desired to intercept, and the sizes of those which are to emerge from the inhaler. There may also be means to define an aperture downstream of the impactor and spaced apart from it, to impose an additional S-shaped deviation on the air flow.

Figure 2:
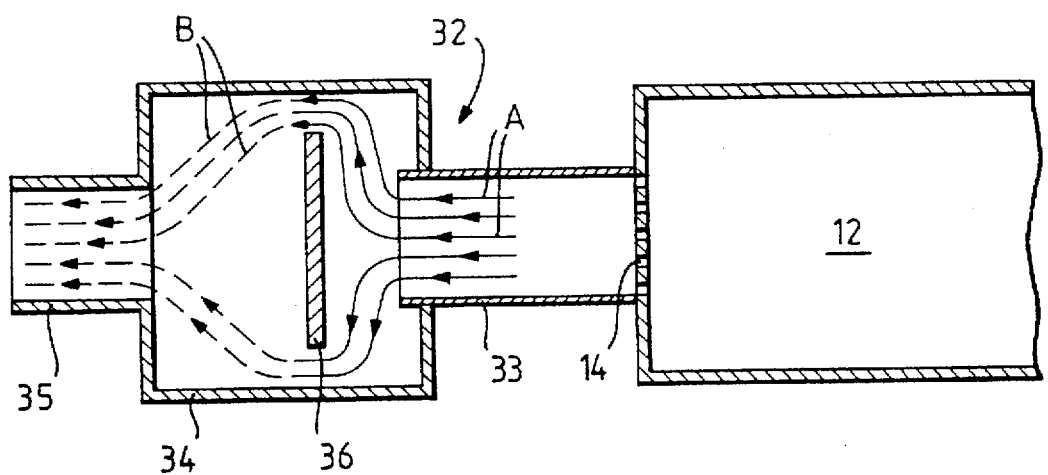
Figure 3:
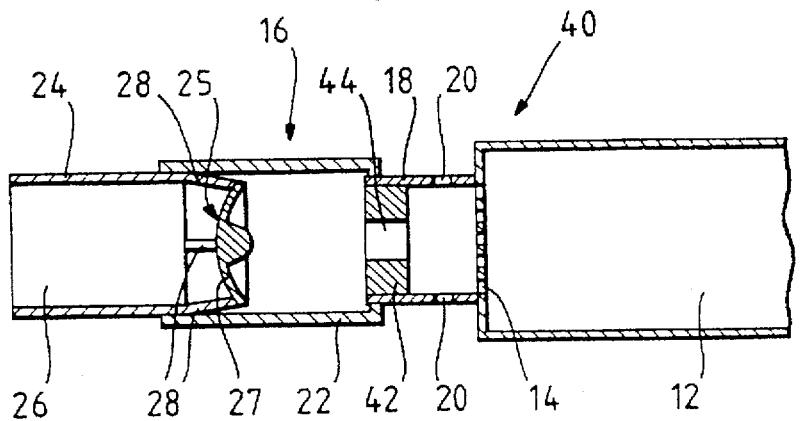
Figure 4:
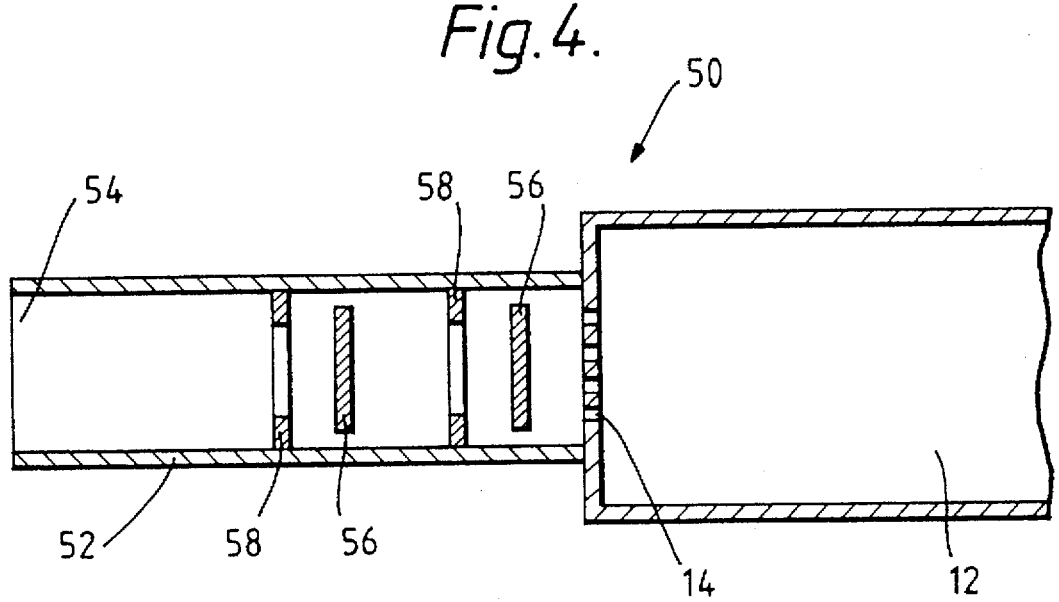
Figure 5:
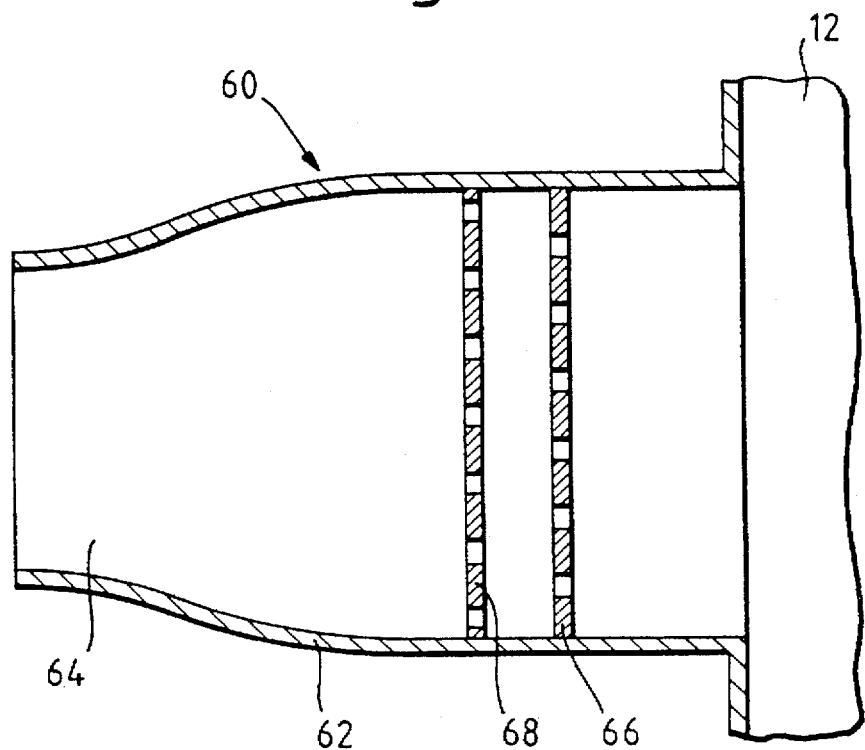

The invention will now be described, by way of example only, and with reference to the accompanying drawings in which:

FIG. 1 shows a longitudinal sectional view of an inhaler;
FIG. 2 shows a diagrammatic longitudinal sectional view of an inhaler;
FIG. 3 shows a modification to the inhaler of FIG. 1;
FIG. 4 shows a longitudinal sectional view of an alternative inhaler; and
FIG. 5 shows a longitudinal sectional view of another alternative inhaler.

Referring to FIG. 1, a powder inhaler 10 comprises a dispensing chamber 12 shown only in part, of conventional design with an air inlet at one end (not shown) and with means (not shown) for introducing a drug powder from a capsule into the chamber 12. At the other end of the chamber 12 is a coarse grid 14 with holes 1.5 mm square separated by 1 mm wide strips. To the chamber 12 outside the grid 14 is connected a three-section duct 16. A first tubular section 18 is of oval cross-section 15 mm by 8 mm; two 2 mm diameter holes 20 are provided at opposite sides. This is connected by a cylindrical linking section 22 of internal diameter 20 mm to a tubular end section 24 of length 23 mm and of circular cross-section 17 mm in internal diameter, with an impactor 25 at one end and defining a mouthpiece 26 at the other. The impactor 25 comprises a circular plate 27 of diameter 15 mm supported by four struts 28 each 7 mm long in front of the aperture defined by the open end of the end section 24; the plate 27 is curved, with a concave surface facing the air stream and with a 5 mm diameter convex hemisphere at the centre.

In use of the inhaler 10 the patient places a drug capsule into the inhaler 10 and operates the means for introducing the dry powder into the chamber dispensing 12. The patient then inhales through the mouthpiece 26. This draws in an air stream through the chamber 12, so the powder is picked up and carried through the grid 14 and along the duct 16; a secondary air stream is drawn in through the holes 20. The air flows-faster through the orifice defined by .the oval tube section 18 than through the linking section 22. The air stream carrying the powder (which may include agglomerates) must then pass the impactor 25 before reaching the patient's mouth. The impactor plate 27 causes the air stream to be diverted to reach the aperture as described in more detail below; substantially all the air flow (at least 80%) is deviated by the presence of the plate 27. Small particles follow the air stream around the edge of the plate 27, but large particles owing to their inertia will impact on the plate 27. They may remain on the plate 27, or rebound towards the grid 14, or be broken up by the impact. Larger particles thrown back will enter a region of turbulent air flow and may be broken up here; alternatively they may impact on the sides of the linking section 22. The small particles produced as a result of these processes will be re-entrained in the air stream and so will reach the patient.

Thus the presence of the impactor 25 causes larger particles either to break up or to remain in the inhaler 10 (on the surface of the plate 27 or the section 22), reducing their delivery to the mouth and throat region of the patient, so reducing side-effects of the drug. Experiments have confirmed that delivery to the mouth and throat is considerably reduced, while there is a corresponding increase in the efficiency of delivery of the drug to the patient's lungs. For example using a Ventolin Diskhaler modified by the provision of the linking section 22 and the end section 24, lung dose was found to rise from 14% of the metered dose to 19–22%, while the mouth/throat dose dropped from 24% of the metered dose to 13–15%. Furthermore the duct sections 22 and 24 and the impactor 25 do not significantly increase the resistance to air flow through the inhaler for the patient.

Referring to FIG. 2, a powder inhaler 30 (represented diagrammatically) comprises a chamber 12 as described above with a grid 14 at one end. Outside the grid 14 is a duct 32 consisting of a narrow first portion 33, a wider portion 34, and finally a narrower mouthpiece 35. A flat impactor plate 36 is supported within the wider portion 34 so as to obstruct and divert the air flow emerging from the first portion 33. The air emerges as a jet from the end of the first portion, and the effect of the plate 36 and the surrounding duct wall is to produce abrupt changes of direction on the air stream, so as indicated by the solid arrows A the air follows S-shaped paths (or, more precisely, two successive L-shaped paths). Larger solid particles do not follow these paths, and are carried by their inertia to hit the plate 36, or to hit the inner surface of the duct portion 34. The air flowing through the peripheral gap around the plate 36 must then undergo changes of direction to reach the mouthpiece (shown by broken arrows B), but these changes are less abrupt, so any particles small enough to be carried beyond the plate 36 can be expected to reach the mouthpiece 35.

The size of the particles which emerge with the air stream from the inhaler clearly depends on the abruptness of the changes of direction that the air has undergone. Considering the effect of the plate 36, the particle diameter d for which half the initially-present particles undergo impaction, referred to as the cut-off diameter, has been found to be given by:

$$d = K(pD/V)^{1/2}$$

where $p = 3.24 \times 10^{-7}$ m$^2$/s

D = diameter of air jet

V = velocity of air jet at the centre and K is a dimensionless constant determined by the cross-sectional shape of the jet and by the ratio of the jet-to-plate spacing to D. If this ratio is 3 the value of K is 0.57 for a rectangular jet and 0.38 for a circular jet. (This distance ratio is desirably between 0.35 and 10, preferably between 1 and 4; the larger this ratio the less sharp is the cut-off between those particle sizes which undergo impaction and those which do not, and K becomes slightly larger. The parameter p is in fact given by 18 times the coefficient of viscosity of air divided by the product of the density of the particle material and a slip factor which is just above one for particles or agglomerates greater than a micron in diameter).

Thus considering the inhaler 10 of FIG. 1, the air jet is defined by the oval duct section 16. If the air flow rate is 60 liters/min then:

V = 8.8 m/s

D = $8 \times 10^{-3}$ m

K = 0.48 (for an oval jet)

Hence the cut-off diameter is about 8.2 microns.

Referring to FIG. 3 there is shown an inhaler 40 which differs from that of FIG. 1 only in including an insert 42 in the end of the duct section 18 remote from the grid 14, the insert 42 defining a tubular orifice 44 for air flow circular in cross-section and of diameter 7.5 mm. With the same air flow of 60 liters/min, the velocity will be greater and the jet diameter less, so the cut-off diameter is less, as follows:

V = 22.6 m/s

D = $7.5 \times 10^{-3}$ m

K = 0.38 so the cut-off diameter is about 3.9 microns. It will be appreciated tha the cut-off diameter can be adjusted to suit a particular drug and a particular application, by using an insert 42 defining a tubular orifice of a suitable diameter, as long as the resistance to air flow is not so large as to lower the air flow rate through the inhaler 40.

In the inhalers of FIGS. 1, 2 and 3 the orifice from which the air jet emerges is sufficiently far from the grid 14 that the spatial flow variations due to the grid 14 are negligible. If the impactor plate is closer to the grid 14 then the characteristic dimension of the air jet, D, will be the width of the grid orifices. For example referring to FIG. 4 an alternative inhaler 50 is shown. It comprises a chamber 12 as described above, with a coarse grid 14 with holes 1.5 mm square at one end. A duct 52 is connected to the chamber 12 outside the grid 14. The duct 52 is of length 55 mm and of elliptical internal cross-section 15 mm by 8 mm, the end remote from the grid 14 providing a mouthpiece 54.

Within the duct 52 are two flat impactor plates 56, each elliptical, 13 mm by 6 mm and supported by three equally spaced struts (not shown), one being 5 mm along the duct 52 from the grid 14, and the other 25 mm from the grid 14. A peripheral ring 58 defining an aperture of the same shape and orientation as the plate 56 but of dimensions 10 mm by 4.5 mm is fixed to the duct wall 5 mm behind each impactor plate 56.

The inhaler 50 is used in the same manner as the inhaler 10, the patient inhaling through the mouthpiece 54 so that an air stream carrying drug powder passes through the grid 14 and along the duct 52. As described above the impactor plates 56 cause larger particles and agglomerates to be broken up or removed from the air stream, so increasing the efficiency of delivery of the drug to the patient's lungs. The grid 14 in this case provides a plurality of orifices, through which the air flows are in parallel. Substantially all the air flow is significantly deviated, by the impactor plates 56 and then by the subsequent peripheral rings 58.

The first impactor plate 56 is close enough to the grid 14 that the width of the air jets is the width of the grid squares, that is 1.5 mm. The grid 14 consists of thirty two such square orifices. With an air flow of 60 liters/min the cut-off particle diameter provided by the first plate 56 is found from:

V = 13.9 m/s

D = $1.5 \times 10^{-3}$ m

K = 0.57 so that the cut-off diameter is about 3.4 microns. The peripheral ring 58 then creates an air jet to impact with the second impactor plate 56. In the embodiment described the particle size distribution is affected only slightly by the flow deviations downstream of the first plate 56; for example for the second impactor plate 58 we have:

V = 21.2 m/s

D = $4.5 \times 10^{-3}$ m

K = 0.48 so the cut-off diameter is about 4.0 microns. Where two impactors are arranged in series, as in the inhaler 50, they might instead be designed so the second impactor produces a smaller cut-off than the first impactor.

Referring now to FIG. 5 there is shown a sectional view to a larger scale of an alternative inhaler 60. This includes a powder dispensing chamber 12 as described above. An oval duct 62 extends 30 mm from the chamber 12; adjacent to the chamber 12 it is 20 mm by 12 mm while at the other end, which forms a mouthpiece 64, it is 15 mm by 8 mm. Within the wider part of the duct 62 are two slotted plates: the first plate 66 defines six slots each 1 mm wide and 12 mm long separated by 2 mm wide plate strips, while the second plate 68 defines seven identical slots separated by 2 mm wide plate strips. The plates 66 and 68 are 3 mm apart, and are such that the slots are staggered relative to those in the other plate, so each slot in the plate 66 is aligned midway between two slots in the plate 68.

The inhaler 60 is used in just the same way as the inhalers described earlier. The air jets created by the slots in the first plate 66 impact with the strips between the slots in the second plate 68. In this case the air jets are rectangular, 12 mm long and 1 mm wide. If the air flow rate is 60 liters/min we have:

$V = 13.9$ m/s $D = 1 \times 10^{-3}$ m $K = 0.57$ so the cut-off diameter is about 2.8 microns.

It will be appreciated that the above embodiments are described by way of example only. In each case the dimensions of the jet-creating orifice and the other dimensions of the impactor can be adjusted to obtain a desired cut-off diameter.

We claim:

1. A dry powder inhaler comprising a dispensing chamber into which dry powder is introduced in operation, a duct and a mouthpiece through which a patient may inspire, the dispensing chamber being connected via the duct to the mouthpiece; the chamber, the duct and the mouthpiece together defining a flow path such that at least the bulk of the inspired air flows through the chamber, then through the duct, and then through the mouthpiece; wherein there is at least one means within the duct to define at least one orifice forming part of the flow path for air, and for particles of the powder carried by the air, there being a portion of the duct downstream of the orifice and the orifice being of narrower width than that portion of the duct downstream thereof; and means to deviate substantially all the air flow through the orifice abruptly along successive L-shaped paths, whereby larger particles of the powder carried by the air flow undergo impaction due to their inertia whereas smaller particles are carried along with the air flow, the deviating means comprising an impactor in the duct between the said orifice and the mouthpiece, the impactor comprising a stationary plate substantially transverse to the flow direction through the orifice but spaced along the duct from the orifice, of larger projected area than the orifice and of such a shape that any line through the orifice extending parallel to the direction of the air flow at the center of the orifice is obstructed by the plate.

2. An inhaler as claimed in claim 1 wherein the ratio between the distance along the duct between the impactor plate and the orifice, and the smallest width of the orifice, is between 0.35 and 10.

3. An inhaler as claimed in claim 2 wherein the said ratio is between 1 and 4.

4. An inhaler as claimed in claim 1 also comprising means within the duct to define an aperture downstream from the impactor plate and spaced apart from it, so as to impose an additional S-shaped deviation on the air flow.

5. An inhaler as claimed in claim 1 wherein the orifice-defining means defines a plurality of orifices through which the air flows are in parallel.

6. An inhaler as claimed in claim 1 comprising within the duct at least two said orifice-defining means spaced apart along the duct, and as many said impactors as there are orifice-defining means.

7. An inhaler as claimed in claim 6 wherein one such orifice and impactor plate is such as to have a larger cut-off diameter than a second orifice and impactor plate nearer to the mouthpiece, the cut-off diameter being the particle diameter for which half the initially-present particles undergo impaction with the impactor plate.

8. An inhaler as claimed in claim 1 wherein the dimensions of an orifice and the distance along the duct between the said orifice and the respective impactor plate are such as to impose a cut-off diameter of between 2 and 10 microns for an air flow of 60 liters/min along the duct, the cut-off diameter being the particle diameter for which half the initially present particles undergo impaction with the impactor plate.

* * * * *